(12) United States Patent
Everett et al.

(10) Patent No.: US 6,522,407 B2
(45) Date of Patent: Feb. 18, 2003

(54) OPTICAL DETECTION DENTAL DISEASE USING POLARIZED LIGHT

(75) Inventors: Matthew J. Everett, Livermore, CA (US); Billy W. Colston, Jr., Livermore, CA (US); Ujwal S. Sathyam, Livermore, CA (US); Luiz B. Da Silva, Danville, CA (US); Daniel Fried, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 52 days.

(21) Appl. No.: 10/100,824

(22) Filed: Mar. 18, 2002

(65) Prior Publication Data

US 2002/0093655 A1 Jul. 18, 2002

Related U.S. Application Data

(63) Continuation of application No. 09/314,848, filed on May 19, 1999, now abandoned.
(60) Provisional application No. 60/116,884, filed on Jan. 22, 1999.

(51) Int. Cl.[7] .................................................. G01J 4/00
(52) U.S. Cl. ........................................ 356/369; 356/364
(58) Field of Search ................................ 356/369, 367, 356/364

(56) References Cited

U.S. PATENT DOCUMENTS

| | | |
|---|---|---|
| 5,321,501 A | 6/1994 | Swanson et al. |
| 5,459,570 A | 10/1995 | Swanson et al. |
| 5,541,413 A | 7/1996 | Pearson et al. |
| 5,570,182 A | 10/1996 | Nathel et al. |
| 6,179,611 B1 | 1/2001 | Everett et al. |
| 6,252,666 B1 | 6/2001 | Mandella et al. |

FOREIGN PATENT DOCUMENTS

WO    WO 98/41158 A1    9/1998

OTHER PUBLICATIONS

Wang, et al., "Characterization of dentin and enamel by use of optical coherence tomography," Applied Optics, US, Optical Society of America, Washington, vol. 38, No. 10, Apr. 1, 1999, pp. 2092–2096.
Colston, et al., "Dental OCT," Optics Express, vol. 3, No. 6, Sep. 14, 1998, pp. 230–238.
Hielscher, et al., "Diffuse backscattering Mueller matrices of highly scattering media," Optics Express vol. 1, No. 3, 441–453 (1997).
Hielscher, et al., "Diffuse backscattering Mueller matrices of highly scattering media," Optics Express vol. 1, No. 3, 441–453 (1997).

(List continued on next page.)

*Primary Examiner*—Michael P. Stafira
(74) *Attorney, Agent, or Firm*—Eddie E. Scott; Alan H. Thompson

(57) ABSTRACT

A polarization sensitive optical imaging system is used to detect changes in polarization in dental tissues to aid the diagnosis of dental disease such as caries. The degree of depolarization is measured by illuminating the dental tissue with polarized light and measuring the polarization state of the backscattered light. The polarization state of this reflected light is analyzed using optical polarimetric imaging techniques. A hand-held fiber optic dental probe is used in vivo to direct the incident beam to the dental tissue and collect the reflected light. To provide depth-resolved characterization of the dental tissue, the polarization diagnostics may be incorporated into optical coherence domain reflectometry and optical coherence tomography (OCDR/OCT) systems, which enables identification of subsurface depolarization sites associated with demineralization of enamel or bone.

43 Claims, 3 Drawing Sheets

OTHER PUBLICATIONS

Feldchtein, et al., "Endoscopic applications of optical coherence tomography," Optics Express, Sep. 14, 1998, vol. 3, No. 6, pp. 257–270.

Danielson, et al., "Guided–wave reflectometry with micrometer resolution," Applied Optics vol. 26, No. 14, pp. 2836–2842 (1987).

Warren, et al., "Imaging and characterization of dental structure using optical coherence tomography," CLEO '98, Tuesday Morning, May 5, 1998, p. 128.

Feldchtein, et al., "In vivo OCT imaging of hard and soft tissue of the oral cavity," Optics Express, Sep. 14, 1998, vol. 3, No. 6, pp. 239–250.

Everett, et al., "Non–Invasive Diagnosis of Early Caries with Polarization Sensitive Optical Coherence Tomography (PS–OCT)," Lawrence Livermore National Laboratory, UCRL–JC–132683 Rev. 1 Preprint, Jul. 8, 1999, 27 pages.

Yougquist, et al., "Optical coherence–domain reflectometry: a new optical evaluation technique," Optics Letters vol. 12, No. 3, pp. 158–160 (1987).

Huang, et al., "Optical Coherence Tomography," Science vol. 254, pp. 1178–1181, Nov. 22, 1991.

Baumgartner, et al., "Optical coherence tomography of dental structures," Proc. SPIE 3248; Lasers in Dentistry IV, John D. Featherstone, Peter Rechmann, Daniel S. Fried, eds., pp. 130–136 (1998).

Rowe, et al., "Polarization–difference imaging—a biologically inspired technique for observation through scattering media," Optics Letters vol. 20, No. 6, pp. 608–610, Mar. 15, 1995.

Lee, et al., "Profilometry with a coherence scanning microscope," Applied Optics vol. 29, No. 26, pp. 3784–3788, Sep. 10, 1990.

OPTICAL DETECTION DENTAL DISEASE USING POLARIZED LIGHT

CROSS-REFERENCE TO RELATED APPLICATIONS

This application is a continuation of U.S. patent application Ser. No. 09/314,848 filed May 19, 1999 titled "Optical Detection of Dental Disease Using Polarized Light," now abandoned. This application claims the benefit of U.S. patent application Ser. No. 09/314,848 filed May 19, 1999, titled "Optical Detection of Dental Disease Using Polarized Light," and U.S. Provisional Application No. 60/116,884 filed Jan. 22, 1999, titled "Dental Explorer," both of which are incorporated herein by this reference.

The United States Government has rights in this invention pursuant to contract No. W-7405-ENG-48 between the United States Department of Energy and the University of California for the operation of Lawrence Livermore National Laboratory.

BACKGROUND OF THE INVENTION

1. Field of the Invention

The present invention relates to the detection of dental disease using polarized light by optically measuring the depolarization of incident light backscattered from dental tissues.

2. Description of Related Art

Dental caries, or tooth decay, is a pathological process of destruction of tooth structure by oral microorganisms, which can lead to tooth loss if untreated. In coronal caries, lesions begin in the enamel and cause demineralization of the enamel. This demineralization changes the scattering properties of the enamel, resulting in chalky or "white spot" lesions visible when the caries occurs on smooth, unstained enamel surfaces. If the carious lesion is detected before it reaches the dentin, remineralization is still possible. After the carious lesion has reached dentin, however, inflammation of the pulp occurs, requiring a filling and leading to serious tooth decay and eventual tooth loss if untreated. Restorative dentistry is most effective when the progression of caries is detected early before it reaches the dentin.

Current techniques for diagnosing caries are visual inspection, mechanical probing with a sharp dental explorer, and radiographic imaging. The tooth can be tactilely and visually explored to determine the presence of indicators of tooth decay such as surface irregularities, crevices, or discoloration. However, the practice of probing all accessible tooth surfaces with a sharp explorer is coming under increased scrutiny since it can further damage enamel already weakened by decay and may also cause cross-contamination between teeth. As tooth decay primarily affects the region of calcium below the tooth surface, detection of caries before significant damage occurs in the tooth is very difficult.

By the time caries is evident under visual and tactile examination of the tooth, the disease is usually in an advanced stage, requiring a filling and occasionally leading to tooth loss. As a consequence of conservative diagnoses and treatment, there are false positives leading to unnecessary drilling and placement of restorations in healthy teeth. Currently there is no accurate device for determining whether restorations are in need of replacement, resulting in enormous costs from the unnecessary replacement of good restorations and complications such as root canals from not replacing defective or aged restorations.

Radiography is often used for detection of cavities, since it provides integrated views of tooth structure that in certain orientations can isolate carious lesions. The sensitivity of radiographic systems, however, is limited by visible changes in film density, making identification of small carious or precarious regions difficult. Since radiographs are two dimensional, precisely locating the position of such decay is impossible. Moreover, due to the orientation of the x-ray imaging, only interproximal lesions (between the teeth) are easily detected, while early occlusal lesions (top of the tooth), are difficult to detect. In addition, radiography uses harmful ionizing radiation.

Given the disadvantages of current detection techniques, a need exists for a device that provides safe, early diagnosis of caries. This invention applies the technique of polarimetry to image dental hard tissue and detect the presence of caries based on the depolarization of incident light. The invention also has the potential for detection of disease in bone.

Polarimetry is a well-established tool for non-invasive material characterization and involves comparison of the polarization states of light before and after the light interacts with the material. The use of polarized light for characterization and imaging of highly scattering media, such as biological tissue, has been studied. The effect of scattering on the polarization state of light has been found to be useful for imaging of surface or subsurface structures in scattering media, and for transmission imaging of deep structures. See Rowe et al., "Polarization-difference imaging—a biologically inspired technique for observation through scattering media", Optics Letters 20:608–610 (1995). It has also been shown that the scattering parameters of turbid tissue, including the scattering coefficient $\mu_s$ and anisotropy factor g, can be determined from diffusely scattered polarized light. See Hielscher et al., "Diffuse backscattering Mueller matrices of highly scattering media", Optics Express 1:441–453 (1997).

Polarimetry may be combined with a second method, optical coherence domain reflectometry (OCDR), which was developed as a high resolution ranging technique for characterization of optical components and was based on bulk optics. See Youngquist et al., "Optical coherence-domain reflectometry: a new optical evaluation technique", Optics Letters 12(3):158–160 (1987). The first fiber optic based OCDR system was constructed by the U.S. National Bureau of Standards for micro-optic technology. See Danielson et al., "Guided-wave reflectometry with micrometer resolution", Applied Optics 26(14):2836–2842 (1987).

OCDR uses a low coherence Michelson interferometer to probe the sample, generating reflection signals as a function of depth. When the probe beam is transversed across the sample, a series of axial scans can be stacked together to form a high-resolution two-dimensional optical coherence tomogram. See Lee et. al, "Profilometry with a coherence scanning microscope", Applied Optics 29(26):3784–3788 (1990). Optical coherence tomography (OCT) was developed to produce cross-sectional images of biological microstructure by combining transverse scanning with a fiber optic OCDR system. See Huang et al., "Optical Coherence Tomography", Science 254:1178–1181 (1991). U.S. Pat. No. 5,321,501 discloses the general means for construction of an OCT system, specifically as it applies to OCT imaging of the eye for diagnosis of ocular diseases. U.S. Pat. No. 5,459,570 discloses OCT imaging of biological tissue, including measurement of tissue optical properties and the use of polarization sensitive OCT (PS-OCT) to measure tissue birefringence. These OCT devices provide imaging in the eye and circulatory system.

PS-OCT has also been used for measuring birefringence in teeth in an unsuccessful attempt at caries detection. This attempt was unsuccessful because caries causes light to become depolarized by changing the scattering coefficient of the enamel rather than significantly affecting the birefringence of the enamel. See Baumgartner et al., "Optical coherence tomography of dental structures", Proc. SPIE 3248; Lasers in Dentistry IV, John D. Featherstone, Peter Rechmann, Daniel S. Fried, eds., pp. 130–136 (1998).

The application of OCT for dental applications was pioneered by the University of California at Lawrence Livermore National Laboratory. U.S. Pat. No. 5,570,182, assigned to the University of California, discloses the use of OCT for diagnosis of dental caries and periodontal diseases. Co-pending U.S. patent application Ser. No. 09/315,000 assigned to the same assignee, describes a dental explorer device for detecting caries and periodontal disease using OCDR, and is incorporated herein by reference. In order for OCT to be practical and convenient for clinicians to use on patients, an OCDR dental device was developed in the form of a hand-held, portable explorer tool for non-invasively probing teeth and other dental tissues. The OCDR explorer was designed to safely and accurately collect intraoral OCT images of dental tissue and microstructure in vivo for evaluation of dental health.

The capabilities of the dental explorer device have been further expanded and improved in the present invention by the incorporation of polarization sensitive diagnostics. The invention uses PS-OCT to measure the depolarization of light associated with optical scattering, rather than changes in polarization state associated with birefringence, to detect demineralization and caries. By taking advantage of the ability of polarimetry to both image tissue and detect changes in its scattering properties, a powerful diagnostic tool has been developed for detection of carious lesions.

SUMMARY OF THE INVENTION

This invention provides an optical technique and dental tool that use polarized light for early, non-invasive, and effective diagnosis of the state and structure of hard biological tissues (e.g., teeth and bone). The invention is particularly suited for detection of precarious and carious lesions, and may be useful for evaluation of dental restorations. The method is based on optically detecting the change in polarization of the incident light backscattered from dental tissues. In particular, the demineralization of tooth enamel that is the precursor to caries disease modifies the scattering properties of the tissue, resulting in depolarization of the incident light, which is then detected by the optical imaging system.

In the present invention, the tooth (or other mineralized tissue) is irradiated with polarized light having a selected or known polarization state; either circular, linear, or elliptical. Light backscattered from the tooth is then analyzed using optical polarimetry to determine its degree of polarization. The tooth can also be irradiated with multiple polarization states sequentially to differentiate between changes in polarization state associated with birefringence and depolarization. Depth-resolved images of the demineralization of the enamel can be obtained based on either the temporal or spatial coherence of the incident light by using optical coherence domain reflectometry or confocal imaging, respectively, and incorporating polarimetry. Depth-resolved information about the depolarization is useful as it enables identification of subsurface precarious and carious lesions and minimizes the effects of fresnel reflections from the front surface of the tooth, which can make the results more difficult to interpret.

The polarization sensitive optical imaging system can incorporate a dental explorer tool, which contains one or more optical fibers that independently couple light from the optical imaging system to the tip of a dental probe. The probe is placed against the tooth (or hard tissue), and light from the fiber at the tip of the probe is directed into the enamel. The light reflected or backscattered from the tissue is then collected by an optical fiber and detected by the optical imaging system. In a preferred embodiment, the polarized light is delivered and collected using a polarization sensitive OCDR system, which provides a single point profile of optical scattering (and thus tissue microstructure) as a function of depth.

The OCDR system consists of a light source split by a beamsplitter or fiber optic coupler into a sample arm and reference arm. Reflected or backscattered light from the tissue is collected in the sample arm and detected by heterodyning with the light in the reference arm. Only the photons in the sample arm that have traveled the same optical path length as the photons in the reference arm (within the coherence length of the source) generate a heterodyne signal. Thus, by varying the path length of the reference beam and recording the amplitude of the heterodyne signal, the OCDR system measures the scattering coefficient of the tissue as a function of depth. By moving the dental probe transversely across the tissue, the clinician can obtain a series of profiles of tissue microstructure. These profiles are combined to form a cross-sectional, or optical coherence tomography (OCT), image of the region of interest in the oral cavity. The polarization sensitive OCDR/OCT systems provide images of polarization state as a function of depth.

The object of this invention is to provide a dental tool that uses the depolarization of incident light to detect changes in the tissue microstructure that are indicative of disease. Another object of the invention is to provide a dental tool that combines polarimetry and optical coherence domain reflectometry. It is further an object of this invention to combine polarimetry with optical coherence tomography to generate depth-resolved images of the degree of polarization of light passing through tissue as a function of tissue depth. The invention uses PS-OCT to measure the depolarization of light associated with optical scattering, rather than effects due to birefringence. This invention is particularly suited to detecting the demineralization of teeth associated with caries, and may be useful for detecting demineralization of other mineralized tissues, such as bone. Other objects and advantages of the present invention will become apparent from the following description and accompanying drawings.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

The present invention is a dental tool and optical method for detection of caries by measuring the depolarization of light backscattered from hard dental tissue, such as enamel. Polarized light is directed at the dental tissue to be examined, and the light backscattered from the tissue is then collected and the change in its polarization state measured. The polarization state of the backscattered or reflected light can be analyzed either using optical polarimetric imaging techniques or using polarization sensitive optical coherence domain reflectometry (PS-OCDR) and optical coherence tomography (PS-OCT) systems, which measure the depolarization as a function of tissue transverse position and depth. The light used for probing the dental tissue is in the visible or near-infrared (e.g., >700 nm), thus avoiding the ionizing radiation used in radiography.

The present invention is particularly useful for detecting precarious and carious lesions. An indicator of caries is demineralization of the enamel, which causes large-angle scattering and changes the scattering coefficient of the enamel. This scattering affects the polarization state of the light scattered or reflected back from the tooth. Specifically, light scattered from normal enamel remains polarized, while light scattered from demineralized enamel becomes depolarized. The invention measures the polarization state, or amount of depolarization, of the backscattered light, thereby detecting the degree of demineralization in the enamel. Optical polarimetry using a CCD camera and polarizers is useful for imaging of surface caries and images a number of teeth simultaneously, while PS-OCDR or PS-OCT systems provide depth resolution, improving the sensitivity of the system to caries and enabling identification of subsurface demineralization sites. Depth-resolved imaging can also be achieved through confocal imaging. Confocal optical imaging systems are known in the art (e.g., see U.S. Pat. RE32,660 to Lindow et al.).

Figure 1:
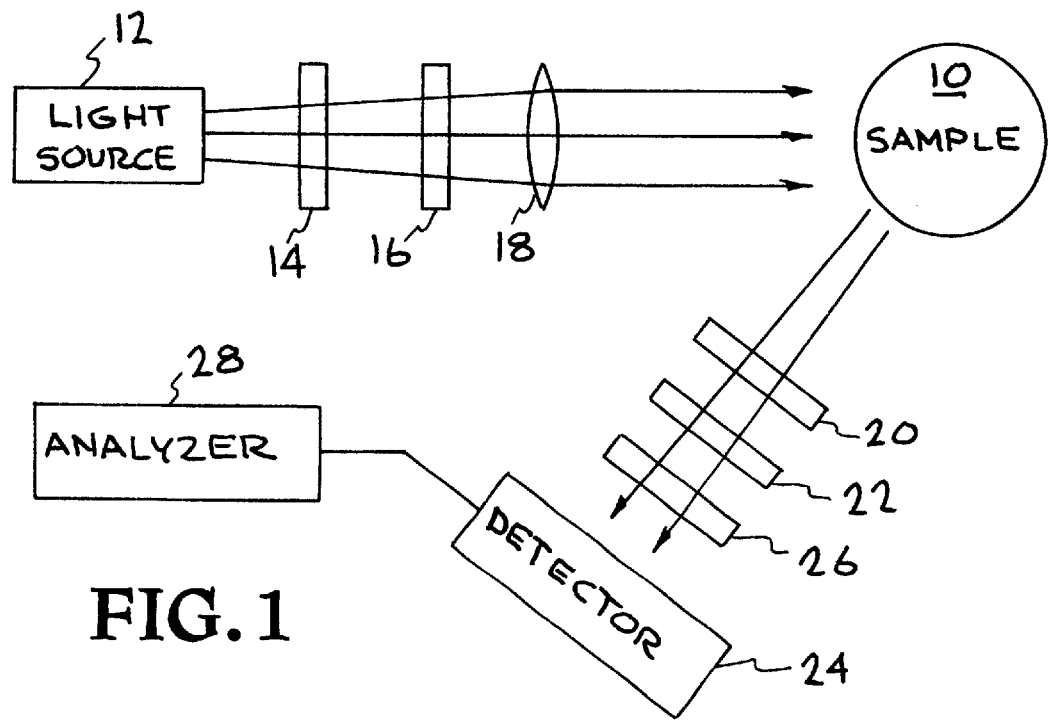
FIG. 1 shows a polarimetric imaging system used in the present invention.

FIG. 1 shows an embodiment of a polarimetric imaging system used in accordance with the present invention. The sample 10, such as a tooth, is illuminated by a low coherence light source 12 followed by a polarizer 14, an optional wave plate 16, and a collimating lens 18. The polarizer 14 and collimator 18 cause an incident beam of polarized light to be focused on the sample 10, while the wave plate 16 makes the polarization state adjustable. The incident beam has a known polarization state. Any polarization state can be used: circularly polarized, elliptically polarized, or linearly polarized. A series of different incident polarization states can also be used sequentially. The use of a series of polarization states makes it possible to discriminate the changes in polarization associated with depolarization from birefringence-induced polarization changes.

The reflected scattered light from the illuminated sample 10 passes through a wave plate 20 and polarizer 22, and then is imaged onto a detector 24, such as a CCD camera or photodetector. An optional optical bandpass filter 26 may be inserted after the polarizer 22, as shown. The bandpass filter 26 is used to select the wavelength band for optimum discrimination between normal enamel and carious lesions. The polarizer/wave plate combination selects the appropriate polarization states to be detected by the detector 24.

The sample is imaged twice by the detector 24, once with the polarizer 22 in front of the detector 24 oriented to pass horizontally polarized light, and once with the polarizer 22 passing vertically polarized light. The two polarization states could also be measured simultaneously, using two detectors or CCD cameras. The two images are processed by an analyzer 28, which includes a computer. A third image is generated by the analyzer 28, which displays the amount of depolarization occurring at each location on the surface of each sample, by taking the ratio or a related mathematical function of the two images (for instance, the difference of the two images over the sum of the two images). If the tooth is illuminated sequentially with a series of polarization states, this process would be repeated for each incident polarization state, and the depolarization is determined based on all of the images. These measurements are ratiometric and thus should be relatively unaffected by environmental factors such as changes in the light intensity. Such a system is easily incorporated into a camera system designed for the oral cavity.

This polarimetric imaging system can detect demineralized enamel at the surface of a sample tooth. In some cases, the enamel at the surface remineralizes as the caries progresses into the tooth towards the dentin, which reduces surface effects of the lesion. X-ray radiography, which uses harmful ionizing radiation, is currently the only available technique for detecting these subsurface lesions. The polarimetric technique of the present invention, when combined with depth-resolved imaging techniques such as optical coherence domain reflectometry (OCDR) and optical coherence tomography (OCT) or confocal imaging, can also detect these subsurface caries.

Figure 2:
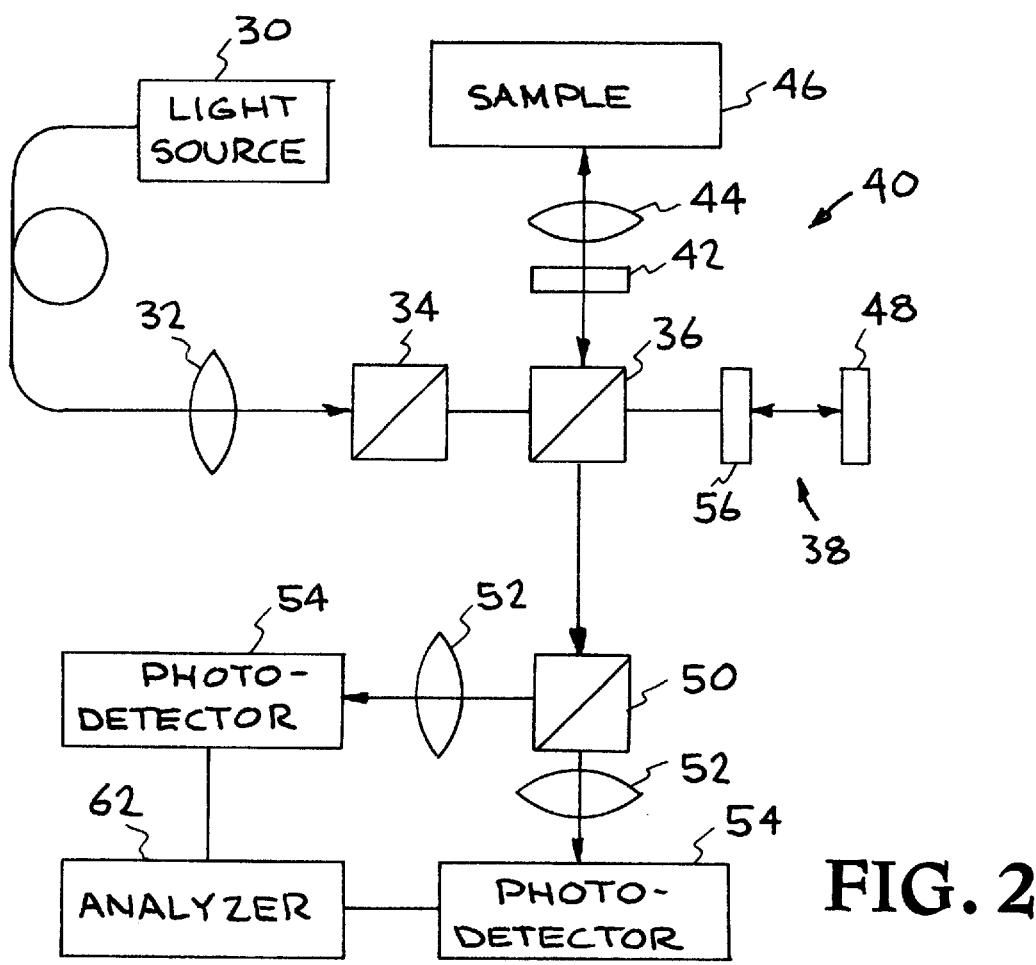
FIG. 2 shows a polarization sensitive optical imaging system using optical coherence domain reflectometry with bulk optics.

FIG. 2 shows an embodiment of a polarimetric, depth-resolved optical imaging system based on OCDR/OCT using bulk optics. This system has a light source 30 that produces an incident beam of light that is collimated using optics 32 and polarized by a polarizer 34. The source 30 is typically a broad bandwidth (on the order of 50 nm) amplified spontaneous emission (ASE) source such as a superluminescent diode or fiber ASE source operating in the visible or near infrared. The polarized light is split by a non-polarizing beamsplitter 36 into a reference arm 38 and a sample arm 40 of a Michelson interferometer. The sample beam may pass through a wave plate 42 and optics 44 before illuminating the area of interest on the sample 46. The wave plate 42 (or retardation plate) in the sample arm 40 controls the state of polarization of the light incident on the sample 46 and makes it possible to illuminate the sample with a series of different polarization states sequentially.

The reference arm 38 provides a variable optical delay. The reference beam is directed to a reference mirror 48, which is translated in the direction of beam propagation to vary the path length. The reflected beam from the reference mirror 48 and the backscattered light from the sample 46 are recombined by the beamsplitter 36. A polarizing cube (or beamsplitter) 50 splits the recombined beam into its horizontal and vertical polarization components, which are then focused by optics 52 and coupled by single mode fibers onto two photodetectors 54. A quarter-wave plate 56 set at 22.5° to the horizontal in the reference arm 38 rotates the linear polarization of the returning light by 45° such that it is split evenly between the two detectors 54. This quarter-wave plate could be replaced with any polarizing optic which causes equal amounts of light to be in the vertical and horizontal polarization states.

The information recorded by the detectors 54 is then processed by an analyzer 62. Depolarization is quantified by the analyzer by measuring the relative intensities of the heterodyned signals in the two orthogonal polarization states. Backscattered light from the tissue is collected in the sample arm and measured as a function of depth in the tissue by varying the reference arm path length while the measuring the heterodyne signal. A heterodyne signal is generated when the light in the sample arm has traveled the same optical path length as the light in the reference arm within the coherence length of the source. Thus, by varying the path length of the reference beam and recording the amplitude of the heterodyne signal on each detector as a function of path length, the OCDR system measures the amount of light backscattered from the tissue and its polarization state as a function of transverse position and depth.

Adding transverse scanning to the sample arm results in a polarization-sensitive OCT system, generating two-dimensional cross-sectional maps of the polarization state of the light within the sample. A series of one-dimensional scans are combined to create two-dimensional intensity and polarization plots. The acquisition times for cross-sectional images are less than one minute, and typically on the order of seconds. This approach provides depth-resolved information about depolarization and therefore facilitates the identification of subsurface sites of demineralization. Transverse scanning mechanisms are described in co-pending U.S. patent application, Hand-Held Dental Imaging Device, Serial No. 60/116885, co-assigned to the same assignee, which is incorporated herein by reference.

An alternative embodiment of the polarization sensitive OCDR/OCT system would eliminate the axial scanning, and instead simply modulate the pathlength of the reference arm a distance on the order of a few microns or less. This system would then measure the depolarization of the incident light backscattered from a fixed depth in the tissue.

The OCDR/OCT system described above for FIG. 2 is a bulk optic system and therefore not easily deployable for in vivo use in a dental office. A more practical system offers ease of use and portability, such as a fiber optic based system. A fiber optic polarization sensitive OCDR/OCT system follows the same principles as the system shown in FIG. 2, but using polarization maintaining (PM) fibers and replacing most of the bulk optic components with in-line fiber optic components.

Figure 3:
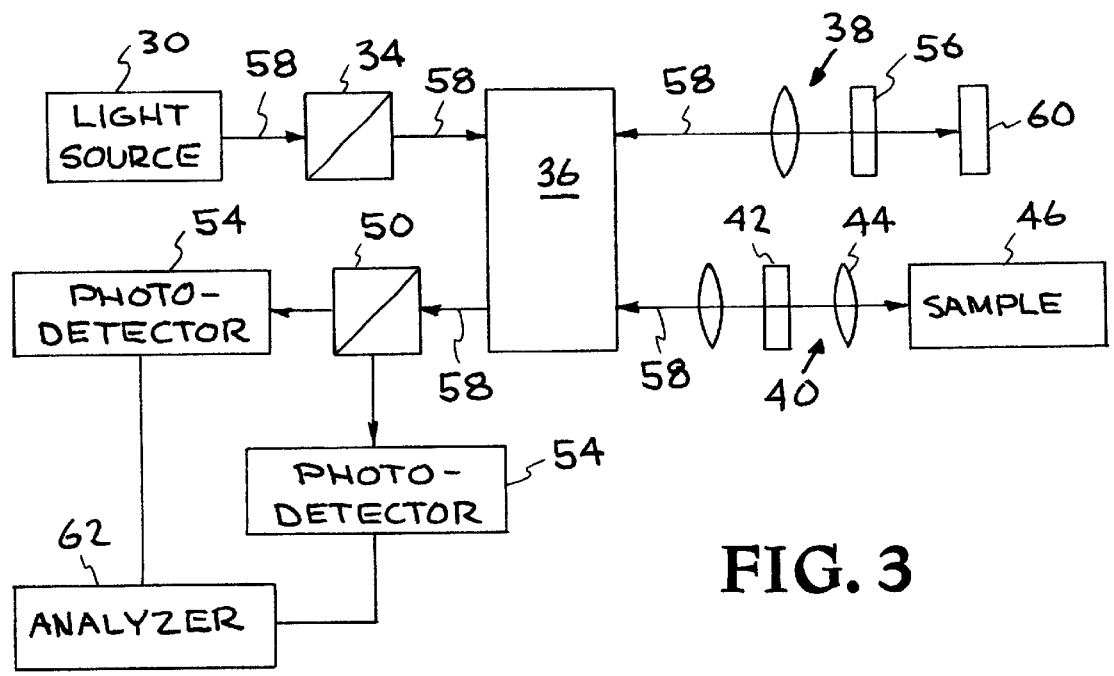
FIG. 3 shows a fiber optic based polarization sensitive optical imaging system used in the present invention.

FIG. 3 shows a diagram of a fiber optic based polarization-sensitive OCDR/OCT system suitable for in vivo measurements. The bulk optic polarizers and beamsplitter shown in FIG. 2 are replaced with an in-line fiber optic coupler or beamsplitter and in-line polarizers, and the free space between the components replaced with PM optical fiber 58. The reference arm length can be varied with a retro-reflector (or mirror) 60 driven by a galvanometer. The detectors, wave plates, and collimating lenses remain the same as in FIG. 2. The only significant alignment required is the coupling of light from the reference arm fiber onto the retro-reflector 60 and then back into the fiber. Even this bulk optic reference arm can be eliminated by using a piezoelectric transducer system to vary the length of the reference arm fiber and/or the sample arm fiber.

The fiber optic based system ensures that the detectors 54 collecting the two polarization states are always identically aligned for the light reflected from the reference arm and the sample arm, greatly enhancing the reliability and ease of use of the system. In addition to improving the reliability of the system, these changes make it possible to use the system for in vivo measurements, as it is possible to use an optical fiber to probe the oral cavity.

Figure 4:
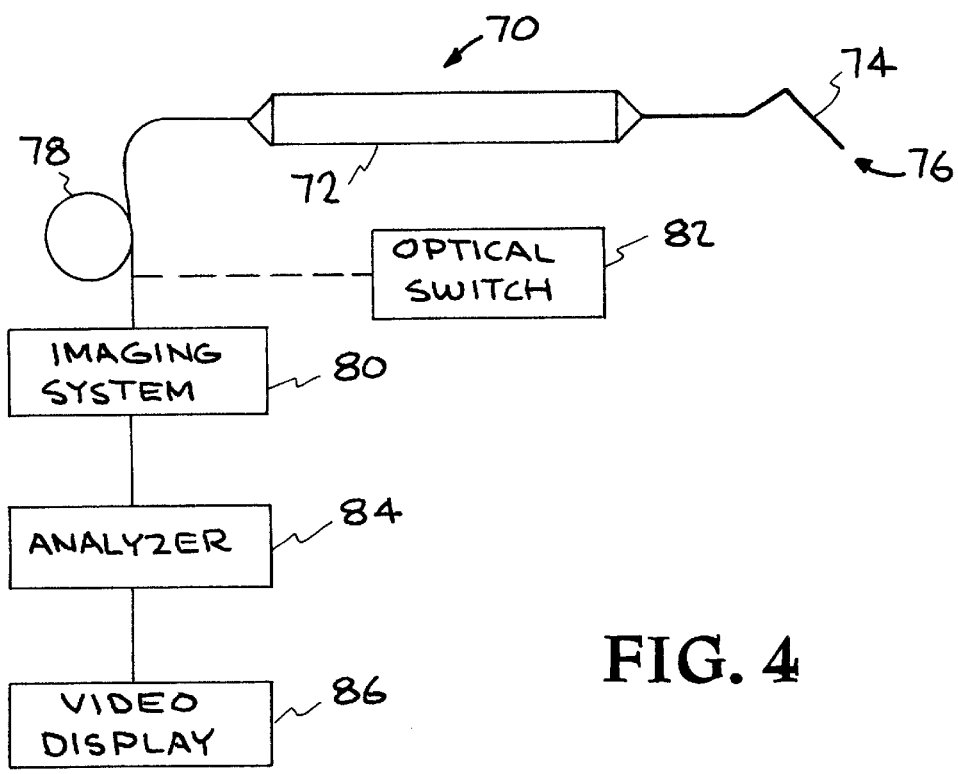
FIG. 4 shows an embodiment of a hand-held fiber optic dental probe according to the present invention.

FIG. 4 shows an embodiment of a hand-held fiber optic dental probe according to the present invention. The probe incorporates an optical fiber that couples to an imaging system, such as a polarimetric imaging system as shown in FIG. 1 having polarizers and a CCD camera. Alternatively, the dental probe optical fiber is the sample arm coupled to a PS-OCDR/OCT system, as shown in FIGS. 2–3. The OCDR/OCT system provides depth-resolved detection of diseased (e.g., carious) lesions wherever the tip of the probe touches the sample tissue (e.g., a tooth). This fiber optic probe for in vivo diagnosis of caries resembles a dental explorer, a device familiar to dental clinicians.

The device 70 comprises a hand-held portion 72 so that the operator can manually manipulate the device, and a probe portion 74 that can be easily inserted into a patient's mouth. The device can be designed so that the probe is manipulated robotically or remotely, in which case a handle for an operator is unnecessary. The shape of the probe portion 74 is designed to comfortably access as much of the oral cavity as possible, and thus may be curved or angled like a conventional dental explorer so that the tip 76 of the probe reaches the posterior portions of the dental cavity. The bends or curves in the probe and optical fiber are limited by the radius of curvature at which significant amounts of light escape from the fiber, typical approximately 0.5 cm.

The device 70 contains a single mode polarization maintaining (PM) optical fiber 78, which independently couples light from an imaging system 80 to the tip 76 of the explorer device 70. Light is emitted from the tip 76 of the device 70 from the distal end of the fiber 78. An optional miniature waveplate can be attached to the end of the fiber to cause the linearly polarized light from the fiber to become circularly polarized. Alternatively, a polarization maintaining (PM) optical fiber can be used, and the fiber can be rotated or twisted to vary the polarization. The rotation can be effected by manually rotating the explorer device or by mechanical means within the explorer device connected to the fiber. When the imaging system is an OCDR/OCT system, the device serves as an extension of the sample arm, and the system provides depth-resolved detection of carious lesions wherever the tip of the explorer device touches a tooth.

Although a single optical fiber device is described in detail, the present invention can readily be modified to accommodate a multi-fiber bundle, and thus references to a single fiber also extend to the use of a plurality of fibers. In a multi-fiber probe, the light from the tip of the device is emitted from the distal end of a plurality of fibers. The fiber optic bundle is connected to an optical switch 82 or optical multiplexer, which is used to switch light between the fibers in the bundle. The optical switch 82 is connected to the imaging system 80. Alternatively, each fiber is connected to separate imaging systems 80.

The probe light emitted from the distal end of the fiber 78 is emitted from the tip 76 of the explorer device 70 and directed at or into the hard tissue, such as enamel, at the appropriate location. The probe tip 76 may be placed next to a tooth, or slipped between a tooth and periodontal tissue. The spot size is typically less than 50 $\mu$m, and can be on the order of 5 $\mu$m. The distal end of the fiber is cut and/or polished at an angle, typically approximately 10 degrees, to eliminate back reflections. The light can also be directed to the tissue through the side of the fiber and probe by angle-polishing the fiber tip at a steeper angle, i.e., near 45 degrees, and then coating the polished surface with a metal such as aluminum. The probe light, which would have been emitted out the end of the fiber 78, is then reflected, thus imaging the tissue next to the fiber tip instead of in front of it.

Alternatively, the light may be focused using one or more small diameter (e.g., millimeter or submillimeter) optical elements or optics, such as gradient index (GRIN) lenses, mirrors, or prisms. The focusing/collection optics may be mounted or attached directly to the end of the PM fiber, or the light may travel through free space from the PM fiber to the optics. If a lens is mounted to the end of the fiber, an index matching ultraviolet curable epoxy may be placed at the fiber/lens interface to minimize refractive index mismatch and reflections.

The probe can be constructed to direct the polarized light at any angle or angles relative to the tip. For example, in a "forward-firing" device, the light is emitted substantially parallel to the fiber, from the very tip of the probe portion. Alternatively, the device can be "side-firing", where the light is emitted from the side of the tip. The light may be redirected or focused to the appropriate location by angle-polishing the end of the fiber or by using small (submillimeter diameter) focusing/collection optics, such as a GRIN lens and/or a prism. The optics may be attached directly to the PM fiber using an index-matching epoxy. The device tip can also be designed to permit light to be emitted from one or more PM fibers in one or more directions at the tip or through a plurality of openings or transparent areas at or near the tip.

The fiber and focusing/collection optics are preferably internal to the handle and probe portions of the explorer device. The probe portion may be a small diameter hollow tube, tapering like a needle at the tip. The light emitted from the end of the fiber may pass through an uncovered opening at or near the tip of the device, or through an opening covered by a window of transparent material, or the tip or probe portion may be made of a transparent material. Since the tip of the probe is in contact with dental tissues and fluids, the tip or probe portion must be detachable and disposable, or capable of being sterilized. Suitable materials for making the probe tip include glass and metals. Alternatively, a transparent, sterilized, disposable cover piece for hygienic purposes can be placed over the tip of the probe portion before insertion into the patient's oral cavity.

Co-pending U.S. patent application, Dental Optical Coherence Domain Reflectometry Explorer, Ser. No. 09/315,000, assigned to the same assignee, is incorporated herein by reference and illustrates various embodiments of the probe portion of a fiber optic dental explorer device.

After the polarized incident beam interacts with the sample (e.g., tooth), the light reflected or backscattered from the tissue is then collected by the same optical fiber and detected by the imaging system 80. The information, i.e., the amount of depolarization, is then processed by an analyzer 84. To serve as a tool for clinicians, the images processed by the analyzer may be displayed on a video display monitor 86 for visual inspection. Alternatively, the analyzer 84 may be programmed to send a signal when the depolarization of the illuminated tissue is within a selected range of values to alert the clinician that diseased tissue may be present. For example, the signal could be auditory, such as a series of beeps, or in the form of a visual display.

If the imaging system is an OCDR system, each measurement provides a single point profile of optical scattering and polarization state as a function of depth. By moving or dragging the dental probe transversely in one direction across a tooth or other tissue, a series of profiles of tissue microstructure are generated. The collected one-dimensional scans are combined by the analyzer to form a depth-resolved, two-dimensional, cross-sectional OCT image of the polarization state of light backscattered from the tooth.

EXAMPLE I

Figure 5:
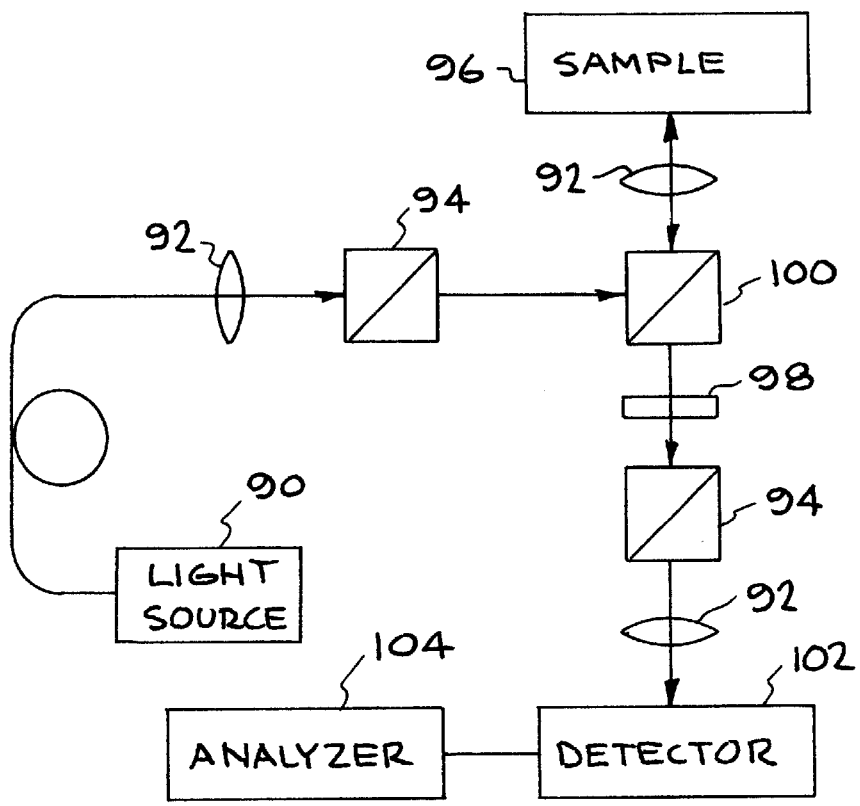
FIG. 5 shows an embodiment of an optical polarimetry imaging system used in the present invention.

A prototype optical polarimetry system as shown in FIG. 5 was built and tested to detect caries using the polarization state of light backscattered from enamel. The fiber coupled source is indicated at 90, lenses are indicated at 92, polarizers are indicated at 94, the sample is indicated at 96, a half-wave plate is indicated at 98, the beamsplitter is indicated at 100, the detector is indicated at 102, and the analyzer to process the data and associated images is indicated at 104. The source was a horizontally polarized superluminescent diode operating at a center wavelength of 1310 nm, with a spectral band of 47 nm. The sample consisted of two juxtaposed 5 mm wide blocks of porcine enamel, one of which was artificially demineralized using an acid bath. The two blocks were oriented at 20 degrees to the normal in the vertical plane to eliminate specular reflections. The sample was scanned transversely across the incident beam from normal enamel surface to the demineralized area.

Figure 6:
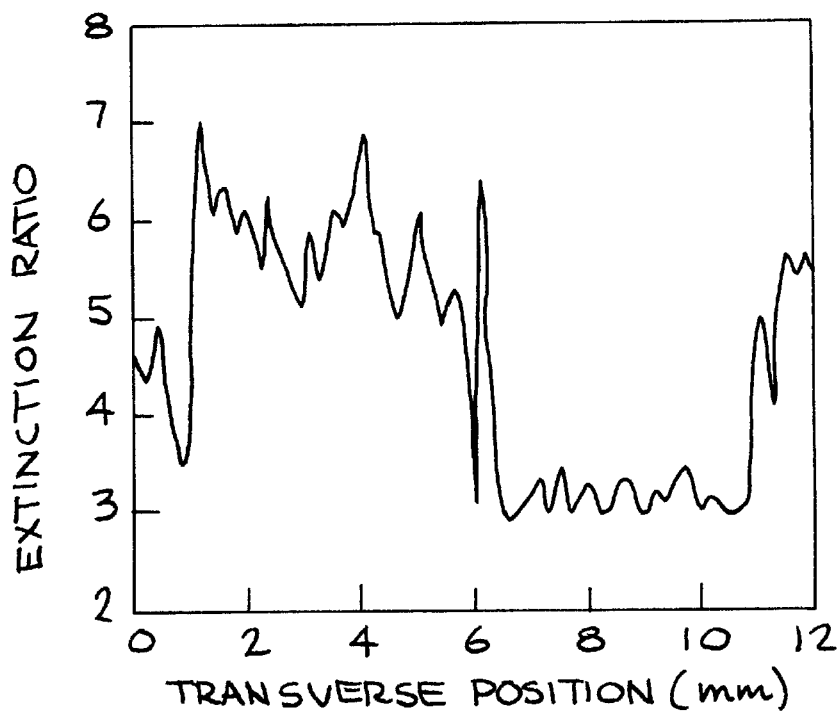
FIG. 6 shows a plot of extinction ratio as a function of transverse position or demineralized tooth enamel and normal enamel.

Depolarization of the scattered light was quantified by the extinction ratio of the relative intensities of vertically and horizontally polarized scattered light. FIG. 6 shows the extinction ratio as a function of transverse position: the ratio of horizontally versus vertically polarized light scattered from the demineralized region of the enamel was approximately half that of the ratio for the normal enamel. This data demonstrates that the polarization state of scattered light is an indicator of demineralization state in enamel.

EXAMPLE II

A bulk optic polarization-sensitive OCT (PS-OCT) system as shown in FIG. 2 was built and tested to generate cross-sectional images of carious lesions. The PS-OCT system used a 15 mW superluminescent diode source operating at a center wavelength of 1310 nm, with a spectral bandwidth of 47 nm (FWHM) which was passed through a polarizer, providing 7.5 mW of horizontally polarized light. By measuring the ratio of the heterodyned signals as a function of depth in the sample, a longitudinal OCDR signal was obtained.

The sample was scanned transversely across the incident beam from the normal enamel surface to the demineralized area, and the longitudinal scans at each transverse position were combined to generate a two-dimensional OCT map of the polarization state of the returning light. The two heterodyned signals can also be combined to generate a polarization-insensitive intensity map. The data showed that although the backscattering intensity was only slightly affected by the demineralization, the polarization state of the scattered light clearly delineated the normal enamel from the carious region due to depolarization.

The polarization-sensitive OCT system was applied to scanning extracted human teeth containing naturally occurring carious lesions in the enamel. The images generated were compared to histological sections of the relevant areas of the tooth. The carious enamel was clearly delineated by the polarization state of the scattered light. Both the histology and the polarization image showed demineralized enamel in the same regions. Vertical stripes seen in the images in the normal enamel are caused by birefringence in the tooth associated with the probe light propagating perpendicular to the crystal axes of the enamel. These results indicated that polarization images in PS-OCT provide accurate information for detection of carious lesions.

The foregoing description of preferred embodiments of the invention is presented for purposes of illustration and description and is not intended to be exhaustive or to limit the invention to the precise form disclosed. Many modifications and variations are possible in light of the above teaching.

What is claimed is:

1. A polarization sensitive optical imaging system for examining a dental tissue of interest, comprising:
   a source of polarized light;
   means for directing an incident beam of polarized light having a known polarization state at the dental tissue;
   means for collecting light backscattered from the dental tissue; and
   means for measuring the degree of depolarization of the backscattered light.

2. The system as recited in claim 1, further comprising means to vary the polarization state of the incident light so that a plurality of sequential beams of incident light having different polarization states can be directed at the dental tissue.

3. The system as recited in claim 2, wherein the means to vary the polarization is selected from the group consisting of a wave plate and a polarization maintaining optical fiber.

4. The system as recited in claim 1, further comprising means for measuring polarization as a function of depth in the dental tissue.

5. The system as recited in claim 4, wherein the means for measuring depth comprises an optical coherence tomography system.

6. The system as recited in claim 4, wherein the means for measuring depth comprises a confocal imaging system.

7. The system as recited in claim 1, further comprising means for measuring polarization at one or more selected points on the dental tissue.

8. The system as recited in claim 7, wherein the means for measuring at the selected points comprises an optical coherence domain reflectometry system.

9. The system as recited in claim 1, further comprising an optical coherence domain reflectometry system.

10. The system as recited in claim 1, wherein the means for measuring the degree of polarization comprises a polarimetry system.

11. The system as recited in claim 1, wherein the means for directing the incident beam comprises an optical fiber.

12. The system as recited in claim 1, wherein the means for collecting the backscattered light comprises an optical fiber.

13. The system as recited in claim 1, wherein the means for directing the incident beam and the means for collecting the backscattered light comprise a single optical fiber.

14. The system as recited in claim 1, wherein the means for directing the incident beam and the means for collecting the backscattered light comprise a plurality of optical fibers.

15. The system as recited in claim 1, wherein the means for directing the incident beam comprises means for directing the incident light in a plurality of directions.

16. The system as recited in claim 1, wherein the means for directing the incident light and the means for collecting the backscattered light comprise an optical fiber and a dental probe containing the optical fiber, wherein the probe is capable of being inserted into an oral cavity.

17. The system as recited in claim 1, wherein the polarization state of the incident beam is selected from the group consisting of circularly polarized, elliptically polarized, and linearly polarized.

18. The system as recited in claim 1, wherein the polarization state of the backscattered light is depolarized relative to the incident light, and further comprising an analyzer that determines the amount of depolarization, wherein the analyzer is operably connected to the means for measuring the depolarization.

19. The system as recited in claim 18, wherein the analyzer sends a signal to a system user when the amount of depolarization is within a selected range of values.

20. The system as recited in claim 18, wherein the analyzer generates an image of depolarization as a function of depth in the dental tissue.

21. The system as recited in claim 18, wherein the analyzer generates an image of depolarization as a function of transverse position on the dental tissue.

22. The system as recited in claim 18, wherein the analyzer generates an image of depolarization as a function of depth and transverse position of the tissue.

23. The system as recited in claim 1, further comprising means to scan the incident beam over the dental tissue.

24. The system as recited in claim 1, wherein the dental tissue comprises a tooth.

25. A method for examining a dental tissue of interest using a polarization sensitive optical imaging system, comprising:
   directing an incident beam of polarized light having a known polarization state at the dental tissue;
   collecting light backscattered from the dental tissue; and
   measuring the degree of depolarization of the backscattered light.

26. The method as recited in claim 25, further comprising sequentially directing a plurality of beams of incident light having different polarization states at the dental tissue.

27. The method as recited in claim 25, further comprising measuring depolarization as a function of depth in the dental tissue.

28. The method as recited in claim 27, wherein measuring depolarization as a function of depth is carried out by optical coherence tomography.

29. The method as recited in claim 27, wherein measuring depolarization as a function of depth is carried out by confocal imaging.

30. The method as recited in claim 25, further comprising measuring depolarization at one or more selected points on the dental tissue.

31. The method as recited in claim 30, wherein measuring depolarization at the selected points is carried out by optical coherence domain reflectometry.

32. The method as recited in claim 25, wherein measuring the degree of polarization is carried out by polarimetry.

33. The method as recited in claim 25, further comprising generating an image of depolarization as a function of transverse position on the dental tissue.

34. The method as recited in claim 25, wherein directing the incident beam and collecting the backscattered light is carried out by at least one optical fiber.

35. The method as recited in claim 25, wherein directing the incident beam comprises directing the incident light in a plurality of directions.

36. The method as recited in claim 25, wherein directing the incident light and collecting the backscattered light is carried out by using at least one optical fiber and a dental probe containing the optical fiber, wherein the probe is capable of being inserted into an oral cavity.

37. The method as recited in claim 25, wherein the incident light has a polarization state selected from the group consisting of circularly polarized, elliptically polarized, and linearly polarized.

38. The method as recited in claim 25, further comprising analyzing the polarization state of the backscattered light relative to the incident light to determine the amount of depolarization.

39. The method as recited in claim 38, further comprising sending a signal to a system user when the amount of depolarization is within a selected range of values.

40. The method as recited in claim 25, further comprising generating an image of depolarization as a function of depth in the dental tissue.

41. The method as recited in claim 25, further comprising generating an image of depolarization as a function of depth and transverse position of the tissue.

42. The method as recited in claim 25, further comprising scanning the incident beam over the dental tissue.

43. The method as recited in claim 25, wherein the dental tissue comprises a tooth.

* * * * *